United States Patent [19]

Pastor et al.

[11] Patent Number: 5,654,455

[45] Date of Patent: Aug. 5, 1997

[54] TRIS-PHOSPHITE LIGANDS AND THEIR USE IN TRANSITIOIN METAL CATALYZED PROCESSES

[75] Inventors: Stephen D. Pastor, Danbury, Conn.; Sai P. Shum, Pleasantville, N.Y.

[73] Assignee: Ciba-Geigy Corporation, Tarrytown, N.Y.

[21] Appl. No.: 576,629

[22] Filed: Dec. 21, 1995

[51] Int. Cl.$^6$ .............................. C07F 9/02; C07F 13/00; C07F 15/00; C07F 7/08

[52] U.S. Cl. .............................. 556/13; 556/479; 556/45; 556/136; 556/138; 558/158

[58] Field of Search .............................. 556/13, 479, 45, 556/136, 138; 558/158

[56] References Cited

U.S. PATENT DOCUMENTS

| | | | |
|---|---|---|---|
| 3,527,809 | 9/1970 | Pruett et al. | 260/604 |
| 4,088,669 | 5/1978 | Malek et al. | 260/448.8 |
| 4,318,845 | 3/1982 | Spivack et al. | 524/91 |
| 4,599,206 | 7/1986 | Billig et al. | 558/85 |
| 4,717,775 | 1/1988 | Billig et al. | 568/454 |
| 4,748,261 | 5/1988 | Billig et al. | 556/404 |
| 4,769,498 | 9/1988 | Billig et al. | 568/454 |
| 4,877,908 | 10/1989 | Petit et al. | 568/814 |
| 5,059,710 | 10/1991 | Abatfoglou et al. | 558/78 |
| 5,090,077 | 2/1992 | Caden et al. | 5/456 |
| 5,276,076 | 1/1994 | Pastor et al. | 524/119 |
| 5,292,785 | 3/1994 | Pasteer | 524/117 |
| 5,331,031 | 7/1994 | Pastor et al. | 524/119 |
| 5,344,860 | 9/1994 | Pastor et al. | 524/119 |
| 5,373,040 | 12/1994 | Pastor et al. | 524/119 |
| 5,405,893 | 4/1995 | Pastor et al. | 524/119 |
| 5,489,635 | 2/1996 | Shum et al. | 524/119 |
| 5,489,636 | 2/1996 | Shum et al. | 524/119 |

OTHER PUBLICATIONS

S. Pastor, Trends in Organometallic Chemistry, 1 (1994) pp. 63–70.
Khan & Martell, Homogeneous Catalysis by Metal Complex, vol. II, pp. 66–75, (Academic Press, 1974).
Tsuji, Org. Chem. vol. 6(2), 95–8 (1993).
Brunner et al., Catal. Asymmetric Synth. 1993, 303–322.
Ojima et al. Asymmetric Synth. vol. 5, 102–146 (1985).
Speier, Adv. Organometal. Chem. vol. 17, 407 (1978).
Marciniec et al. J. Organomet. Chem. vol. 446 (1–2) 15–23 (1993).

*Primary Examiner*—Porfirio Nazario-Gonzalez
*Attorney, Agent, or Firm*—Luther A. R. Hall

[57] ABSTRACT

Catalyst systems which comprise a transition metal and a tris(organophosphite) ligand are particularly effective as catalysts for hydrosilation reactions.

15 Claims, No Drawings

TRIS-PHOSPHITE LIGANDS AND THEIR USE IN TRANSITIOIN METAL CATALYZED PROCESSES

The instant invention pertains to novel catalysts which comprise a transition metal and a tris(organophosphite) ligand which are useful in transition metal catalyzed processes, particularly hydrosilation reactions.

BACKGROUND OF THE INVENTION

The use of organic transition metal ligand complex catalysts is well-known in the art for the addition of a silicon hydrogen bond to olefins, acetylenes, aldehydes and ketones in the hydrosilation process as described by Khan and Martell, Homogeneous Catalysis by Metal Complex, Vol II (Academic Press, 1974), p. 66, and later by Speier, Adv. Organometal. Chem., 17, 407 (1978).

Recent reviews of catalytic hydrosilation using transition metal-phosphorus ligand catalysts were compiled by Brunner et at., Catal. Asymmetric Synth. 1993, 303–322; Tsuji, Org. Chem. 6(2), 95–8 (1993); Marciniec et al., J. Organnomet. Chem. 446(1–2), 15–23 (1993) and Ojima et al., Asymmetric Synth. 5, 102–146 (1985).

However, most ligands described in the aforementioned reviews are phosphine ligands A few examples are presented using phosphites as transition metal ligands in hydrosilation reactions. Recently Buono et al. described in U.S. Pat. Nos. 4,877,908 and 5,090,077 the use of aminoalkyl phosphinities as ligands for transition metal catalysts for symmetric hydrosilation. However, aminoalkyl phosphites are not disclosed. The use of monophosphites and bisphosphites as ligands for transition metals in hydroformylation reactions are reported by Pruett et al. in U.S. Pat. No. 3,527,809 and by Billig et al. in U.S. Pat. Nos. 4,717,775; 4,748,261; 5,059,710 and 5,292,785.

None of these references disclose or suggest the instant invention which is a class of novel tris(organophosphite) ligands for transition metals, a novel class of tris (organophosphite)-transition metal complexes and the use of said complexes as catalysts for hydrosilation reactions.

DETAILED DISCLOSURE

The instant invention pertains to a transition metal ligand complex catalyst system which comprises (a) a transition metal selected from Group VIIB, VIII or IB of the periodic table;

and (b) a tris(organophosphite) ligand of formula I

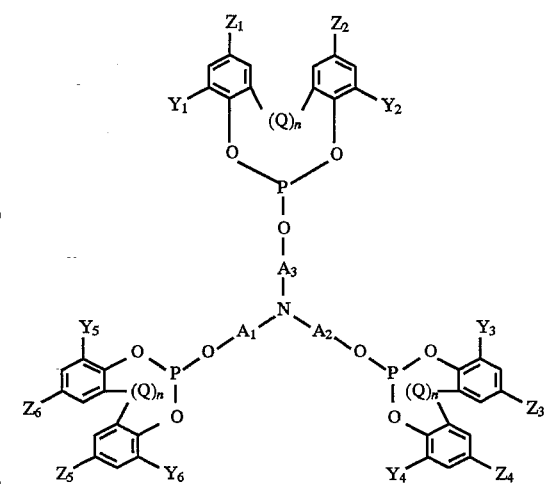

wherein
n is zero or 1;
when n is zero, Q is a direct bond;
when n is 1, Q is —$CR_1R_2$— where $R_1$ and $R_2$ are independently hydrogen, straight or branched chain alkyl of 1 to 18 carbon atoms, phenyl tolyl or anisyl;

$Y_1$, $Y_2$, $Y_3$, $Y_4$, $Y_5$, $Y_6$, $Z_1$, $Z_2$, $Z_3$, $Z_4$, $Z_5$ and $Z_6$ are independently hydrogen, straight or branched chain alkyl of 1 to 18 carbon atoms, bicycloalkyl of 7 to 10 carbon atoms, phenyl, benzyl, 1-phenethyl, cyclohexyl, 1-methylcyclohexyl, cyano, halogen, nitro trifluoromethyl, hydroxy, amino, alkanoyl of 2 to 18 carbon atoms, alkoxy of 1 to 18 carbon atoms or $E_1E_2E_3Si$— where $E_1$, $E_2$ and $E_3$ are independently hydrogen, alkyl of 1 to 4 carbon atoms or phenyl; and $A_1$, $A_2$ and $A_3$ are independently straight or branched chain alkylene of 1 to 18 carbon atoms, phenylene, tolylene, anisylene, cycloalkylene of 5 to 6 carbon atoms, or a branched chain alkylene of 3 to 8 carbon atoms having an asymmetric stereocenter.

Preferably, the transition metal is selected from Group VIII of the periodic table; most preferably the transition metal is rhodium or platinum.

Preferably, when n is 1, Q is —$CR_1R_2$— where $R_1$ and $R_2$ are independently hydrogen, alkyl of 1 to 8 carbon atoms or phenyl. Most preferably, $R_1$ is hydrogen, and $R_2$ is hydrogen, methyl or phenyl.

Preferably, $Y_1$, $Y_2$, $Y_3$, $Y_4$, $Y_5$ and $Y_6$ are alkyl of 1 to 8 carbon atoms or 1-phenethyl. Most preferably, $Y_1$, $Y_2$, $Y_3$, $Y_4$, $Y_5$ and $Y_6$ are each tert-butyl.

Preferably, $Z_1$, $Z_2$, $Z_3$, $Z_4$, $Z_5$ and $Z_6$ are alkyl of 1 to 8 carbon atoms or 1-phenethyl. Most preferably, $Z_1$, $Z_2$, $Z_3$, $Z_4$, $Z_5$ and $Z_6$ are each methyl or tert-butyl.

Preferably, $A_1$, $A_2$ and $A_3$ are independently straight or branched chain alkylene of 1 to 8 carbon atoms, phenylene or cyclohexylene. Most preferably, $A_1$, $A_2$ and $A_3$ are each ethylene, —$CH(CH_3)CH_2$—, (S)—(—$CH(CH_3)CH_2$—) or (R)—(—$CH(CH_3)CH_2$—).

When any of $R_1$, $R_2$, $Y_1$ to $Y_6$ and $Z_6$ to $Z_6$ are alkyl, they are, for example, methyl, ethyl, isopropyl, n-butyl, sec-butyl, tert-butyl, isoamyl, tert-amyl, n-hexyl, 2-ethylhexyl, isooctyl, n-octyl, tert-octyl, nonyl, decyl undecyl, lauryl, tridecyl, tetradecyl, hexadecyl, heptadecyl, octadecyl, eicosyl, tricontyl and branched isomers thereof.

When $A_1$ to $A_3$ are alkylene, they are, for example, methylene, ethylene, trimethylene, propylene, tetramethylene, butylene, hexamethylene and octamethylene.

Another aspect of the instant invention is the use of the transition metal ligand complex catalyst system described above as the catalyst for the hydrosilation of ketones, aldehydes or other compounds containing an ethylenically unsaturated moiety.

The hydrosilation reaction conditions are known in the art, but the use of the instant ligands in such a reaction is novel. Normally phosphites are not robust ligands under typical catalytic conditions and phosphine derivatives are commonly used as such ligands. However, because of the steric hindrance in the compounds of formula I, the instant phosphite ligands possess sufficient stability to be used in the instant process.

Yet another aspect of this invention is the preparation of novel transition metal from Group VIII complexes with tris(organophosphite) ligands, preferably optically pure tris (organophosphite) and catalyst precursor solutions thereof.

The synthesis of optically pure materials is important in the pharmaceutical industry where drug activity often depends on the specific chiral structure of the molecule involved. The same is also true with free chemicals such as fragrances and sweeteners or with agricultural chemicals. In this context, the optically pure phosphites of formula I can be used in catalytic quantities along with transition metals to prepare optically pure pharmaceutical intermediates or products. This is summarized by S. D. Pastor, Trends Organometallic Chem. 1, 63 (1994) where it is stated that catalytic processes, besides their ubiquitous occurrence in nature, are commonplace in the laboratory and play a particularly crucial role in the chemical and petroleum industries. Additionally, catalytic systems serve a vital role in protecting the environment, for example, in the reduction of atmospheric emissions from automobiles. The importance of chirality in nature has led to a sizable effort to develop methodology for asymmetric synthesis. The fact that a biological receptor site can bind differentially a particular enantiomer (chiral recognition) has placed significant importance on asymmetric processes in the pharmaceutical and agricultural industries. The manufacture of the correct biologically active enantiomer is desirable not only because the other enantiomer may be less effective or inactive, but may be antagonistic or even toxic. Of particular importance are asymmetric reactions whose diastereo- and enantio-selectivity are derived through the use of catalytic quantities of chiral transition-metal catalysts.

Still another aspect of the instant invention is a process for the enantio-selective hydrosilation of ketones, aldehydes or unsaturated compounds using a catalyst system comprising a transition metal from Group VIII of the periodic table and an optically active phosphite of formula I.

The following examples are for illustrative purposes only and are not to be construed to limit the scope of the instant invention in any manner whatsoever.

EXAMPLE 1

1,1',1"-Nitrilotri-(S,S,S)-2-propanoltris-[2,2'-bis(4,6-di-tert-butylphenyl)phosphite]

Into a solution of 1.5 g (9.1 mmol) of (S,S,S)-tris-2-propanolamine, 3.8 mL (27 mmol) of triethylamine in 20 mL of toluene is added a solution of 13 g (27 mmol) of 6-chloro-2,4,8,10-tetra-tert-butyl-dibenzo[d,f][1,3,2]dioxaphosphepin in 50 mL of toluene at ambient temperature. After 16 hours of stirring at ambient temperature, the reaction mixture is filtered and the flitrate concentrated to 15 g of a crude oil. The crude product is triturated with 100 mL of acetonitrile to give 10 g of an off-white solid. The crude solid is recrystallized with 100 mL of an acetonitrile/toluene mixture (8/2 by volume) to give the 7 g (51% yield) of the title compound as a crystalline solid melting at 187°–188° C.

EXAMPLE 2

1,1',1"-Nitrilotri-(R,R,S)-2-propanoltris-[2,2'-bis(4,6-di-tert-butylphenyl)phosphite]

The procedure of Example 1 is repeated using 1.85 g (9.7 mmol) of (R,R,S)-tris-2-propanolamine, 4 mL (29.1 mmol) of triethylamine and 13.8 g (29.1 mmol) of 6-chloro-2,4,8,10-tetra-tert-butyl-dibenzo[d,f][1,3,2]dioxaphosphepin in 60 mL of toluene to give 15 g of crude solid, Recrystallizing the solid with 100 mL of an acetonitrile/toluene mixture (9:1 by volume) gives 11 g (73% yield) of the title compound as a crystalline product melting at 180°–184° C.

EXAMPLE 3

1,1',1"-Nitrilotri-2-propanoltris-[2,2'-bis(4,6-di-tert-butylphenyl)phosphite]

The procedure of Example 1 is repeated using 1.34 g (7 mmol) of a racemic mixture of tris-2-propanolamine, 3 mL (21 mmol) of triethylamine and 10 g (21 mmol) of 6-chloro-2,4,8,10-tetra-tert-butyl-dibenzo[d,f][1,3,2]dioxaphosphepin in 60 mL of toluene to give 11 g of a crude solid. The product is purified by flash chromatography (1% ethyl acetate/hexane; silica gel) to give 3 g (28.5% yield) of the title product as a crystalline product melting at 150°–155° C.

EXAMPLE 4

Into a solution of 1.17 mL (10 mmol) of acetophenone, 1.86 mL (10 mmol) of diphenylsilane in 11 mL of toluene is added 10 mL of a yellow solution prepared separately by mixing 15 mg (0.0609 mmol) of (1,5-eycloocmdiene) rhodium (I) chloride dimer and 219 mg (0.1452 mmol) of 1,1',1"-nitrilotri-(S,S,S)-2-propanoltris-[2,2'-bis(4,6-tert-di-tert-butylphenyl)phosphite]in 10 mL of toluene. After stirring for six hours at ambient temperature, a mixture of 5 mL of 2N aqueous potassium hydroxide and 7 mL of methanol is added to the reaction mixture. The reaction mixture is then extracted with diethyl ether (3×3 mL) and the combined ether extracts is dried over anhydrous magnesium sulfate. The dried extract is then concentrated to a yellow oil. The oil is dissolved in 3 mL of hexane. Any solid precipitate is removed by filtration and the filtrate is concentrated to 0.69 g of product as an off-white liquid (57% yield). The enantiomeric excess of (R)-phenethyl alcohol (41%) is determined by the addition of equal molar amount of the chiral solvating agent (R)-(-)2,2,2-trifluoro-1-(9-anthryl)ethanol and comparison of $^1$H NMR to authentic samples of both (R) and (S) phenethyl alcohol.

EXAMPLE 5

The procedure of Example 4 is repeated using 1.17 mL (10 mmol) of acetophenone, 1.86 mL (10 mmol) of diphenylsilane, 15 mg of (0.0609 mmol) of (1,5-cyclooctadiene)rhodium (I) chloride dimer and 219 mg (0.1452 mmol) of 1,1',1"-nitrilotri-(R,R,S)-2-propanoltris-[2,2'-bis(4,6-di-tert-butylphenyl)phosphite] in 21 mL of toluene. The yield of phenethyl alcohol is 45% with enantiomeric excess of 5%.

EXAMPLE 6

The procedure of Example 4 is repeated using 1.17 mL (10 mmol) of acetophenone, 1.86 mL (10 mmol) of diphenylsilane, 15 mg of (0.0609 mmol) of (1,5-cycloocmdiene)rhodium (I) chloride dimer and 219 mg (0.1452 mmol) of 1,1',1"-nitrilotri-2-propanoltris-[2,2'-bis (4,6-di-tert-butylphenyl)phosphite] in 21 mL of toluene. The yield of phenethyl alcohol is 54%.

EXAMPLE 7

The procedure of Example 4 is repeated using 1.17 mL (10 mmol) of acetophenone, 1.86 mL (10 mmol of diphenylsilane, 15 mg (0.0609 mmol) of (1,5-cyclooctadiene)rhodium (I) chloride dimer and 212 mg (0.1452 mmol) of 1,1',1"-nitrilo-triethanoltris-[2,2'-bis(4,6-di-tert-butylphenyl)phosphite] in 21 mL of toluene. The yield of phenethyl alcohol is 60%.

EXAMPLE 8

The procedure of Example 4 is repeated using 1.17 mL (10 mmol) of acetophenone, 1.86 mL (10 mmol) of diphenylsilane, 15 mg (0.0609 mmol) of (1,5-cyclo-octadiene)rhodium (I) chloride dimer and 216 mg (0.1452 mmol) of 1,1',1"-nitrilo-triethanoltris-[2,2'-ethylidene-bis(4,6-di-tert-butylphenyl)phosphite] in 21 mL of toluene. The yield of phenethyl alcohol is 44%.

EXAMPLE 9

The procedure of Example 8 is repeated with (1,5-cyclooctadiene)rhodium (I) chloride dimer being replaced by an equivalent amount of bis(acetonitrile)platinum (II) chloride.

EXAMPLE 10

The procedure of Example 4 is repeated using 1.17 mL (10 mmol) of acetophenone, 1.86 mL (10 mmol) of diphenylsilane, 49.26 mg (0.2 mmol) of (cycloocta-1,5-diene)rhodium (I) chloride dimer and 718.84 mg (0.477 mmol) of 1,1',1"-nitrilotri-(S,S,S)-2-proanoltris-[2,2'-bis(4,6-di-tert-butylphenyl)phosphite] in 10 mL of toluene. The yield of phenethyl alcohol is 77% with enantiomeric excess of 82%.

What is claimed is:

1. A transition metal ligand complex catalyst system which comprises
   (a) a transition metal selected from Group VIIB, VIII or IB of the periodic table; and
   (b) a tris(organophosphite) ligand of formula I

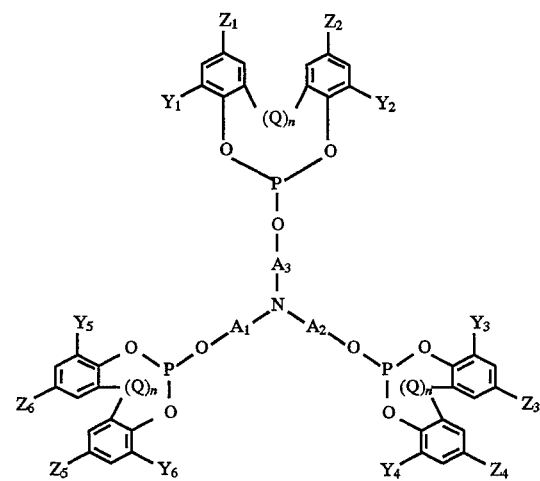

wherein n is zero or 1;

when n is zero, Q is a direct bond;

when n is 1, Q is —$CR_1R_2$ where $R_1$ and $R_2$ are independently hydrogen, straight or branched chain alkyl of 1 to 18 carbon atoms, phenyl tolyl or anisyl;

$Y_1$, $Y_2$, $Y_3$, $Y_4$, $Y_5$, $Y_6$, $Z_1$, $Z_2$, $Z_3$, $Z_4$, $Z_5$ and $Z_6$ are independently hydrogen, straight or branched chain alkyl of 1 to 18 carbon atoms, bicycloalkyl of 7 to 10 carbon atoms, phenyl, benzyl, 1-phenethyl, cyclohexyl, 1-methylcyclohexyl, cyano, halogen, nitro trifluoromethyl, hydroxy, amino, alkanoyl of 2 to 18 carbon atoms, alkoxy of 1 to 18 carbon atoms or $E_1E_2E_3Si$— where $E_1$, $E_2$ and $E_3$ are independently hydrogen, alkyl of 1 to 4 carbon atoms or phenyl; and $A_1$, $A_2$ and $A_3$ are independently straight or branched chain alkylene of 1 to 18 carbon atoms, phenylene, tolylene, anisylene, cycloalkylene of 5 to 6 carbon atoms, or a branched chain alkylene of 3 to 8 carbon atoms having an asymmetric stereocenter.

2. A catalyst system according to claim 1 wherein the transition metal is selected from Group VIII of the periodic table.

3. A catalyst system according to claim 2 wherein the transition metal is rhodium or platinum.

4. A catalyst system according to claim 1 where in the compound of formula I, n is 1, and Q is —$CR_1R_2$ where $R_1$ and $R_2$ are independently hydrogen, alkyl of 1 to 8 carbon atoms or phenyl.

5. A catalyst system according to claim 4 wherein $R_1$ is hydrogen, and $R_2$ is hydrogen, methyl or phenyl.

6. A catalyst system according to claim 1 where in the compound of formula I, $Y_1$, $Y_2$, $Y_3$, $Y_4$, $Y_5$ and $Y_6$ are alkyl of 1 to 8 carbon atoms or 1-phenethyl.

7. A catalyst system according to claim 6 wherein $Y_1$, $Y_2$, $Y_3$, $Y_4$, $Y_5$ and $Y_6$ are each tert-butyl.

8. A catalyst system according to claim 1 where in the compound of formula I, $Z_1$, $Z_2$, $Z_3$, $Z_4$, $Z_5$ and $Z_6$ are alkyl of 1 to 8 carbon atoms or 1-phenethyl.

9. A catalyst system according to claim 8 wherein $Z_1$, $Z_2$, $Z_3$, $Z_4$, $Z_5$ and $Z_6$ are each methyl or tert-butyl.

10. A catalyst system according to claim 1 where in the compound of formula I, $A_1$, $A_2$ and $A_3$ are independently straight or branched chain alkylene of 1 to 8 carbon atoms, phenylene or cyclohexylene.

11. A catalyst system according to claim 10 wherein $A_1$, $A_2$ and $A_3$ are each ethylene, —$CH(CH_3)CH_2$—, (S)—(—CH(CH[<i]nf3)CH_2$—) or (R)—(—$CH(CH_3)CH_2$—).

12. A process for hydrosilation of ketones, aldehydes or other compounds containing an ethylenically unsaturated double bond which comprises reacting the ketone, aldehyde or unsaturated compound with a silane compound in the presence of a transition metal ligand complex catalyst system according to claim 1.

13. The optically active phosphite which is
   (a) 1,1',1"-nitrilotri-(S,S,S)-2-propanoltris-[2,2'-bis(4,6-di-tert-butylphenyl)phosphite], or
   (b) 1,1',1"-nitrilotri-(R,R,S)-2-propanoltris-[2,2'-bis(4,6-di-tert-butylphenyl)phosphite.

14. A process for enantio-selective hydrosilation of ketones, aldehydes or other compounds containing an ethylenically unsaturated double bond which comprises using a catalyst system comprising a transition metal from Group VIII of the periodic table and an optically active phosphite of formula I

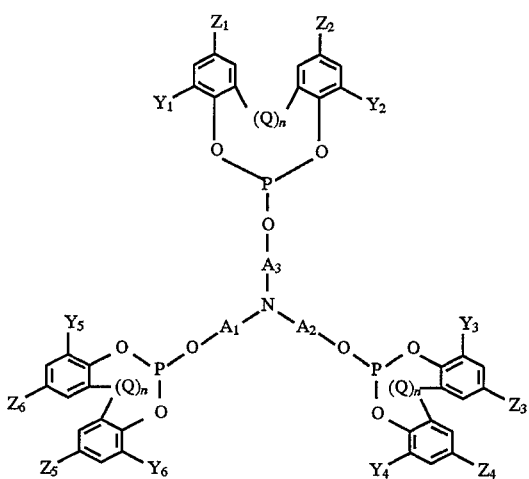

(I)

wherein n is zero or 1;

when n is zero, Q is a direct bond;

when n is 1, Q is —$CR_1R_2$ where $R_1$ and $R_2$ are independently hydrogen, straight or branched chain alkyl of 1 to 18 carbon atoms, phenyl tolyl or anisyl;

$Y_1$, $Y_2$, $Y_3$, $Y_4$, $Y_5$, $Y_6$, $Z_1$, $Z_2$, $Z_3$, $Z_4$, $Z_5$ and $Z_6$ are independently hydrogen, straight or branched chain alkyl of 1 to 18 carbon atoms, bicycloalkyl of 7 to 10 carbon atoms, phenyl, benzyl, 1-phenethyl, cyclohexyl, 1-methylcyclohexyl, cyano, halogen, nitro trifluoromethyl, hydroxy, amino, alkanoyl of 2 to 18 carbon atoms, alkoxy of 1 to 18 carbon atoms or $E_1E_2E_3Si$— where $E_1$, $E_2$ and $E_3$ are independently hydrogen, alkyl of 1 to 4 carbon atoms or phenyl; and $A_1$, $A_2$ and $A_3$ are independently straight or branched chain alkylene of 1 to 18 carbon atoms, phenylene, tolylene, anisylene, cycloalkylene of 5 to 6 carbon atoms, or a branched chain alkylene of 3 to 8 carbon atoms having an asymmetric stereocenter.

15. A process according to claim 14 wherein the optically active phosphite is (a) 1,1',1"-nitrilotri-(S,S,S)-2-propanoltris-[2,2'-bis(4,6-di-tert-butylphenyl)phosphite], or (b) 1,1',1"-nitrilotri-(R,R,S)-2-propanoltris-[2,2'-bis(4,6-di-tert-butylphenyl)phosphite].

* * * * *